(12) United States Patent
Farrow et al.

(10) Patent No.: US 8,257,566 B2
(45) Date of Patent: Sep. 4, 2012

(54) NANOTUBE DEVICE AND METHOD OF FABRICATION

(75) Inventors: Reginald C. Farrow, Somerset, NJ (US); Zafar Iqbal, Morristown, NJ (US); Amit Goyal, Kearny, NJ (US); Sheng Liu, Harrison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 13/162,163

(22) Filed: Jun. 16, 2011

(65) Prior Publication Data

US 2011/0240480 A1  Oct. 6, 2011

Related U.S. Application Data

(62) Division of application No. 11/765,735, filed on Jun. 20, 2007, now Pat. No. 7,964,143.

(51) Int. Cl.
*C25B 7/00* (2006.01)
(52) U.S. Cl. .......................... 204/450; 977/842
(58) Field of Classification Search .................. 204/450; 977/842
See application file for complete search history.

(56) References Cited

U.S. PATENT DOCUMENTS

| | | |
|---|---|---|
| 6,515,325 B1 | 2/2003 | Farnworth et al. |
| 6,566,704 B2 | 5/2003 | Choi et al. |
| 6,616,497 B1 | 9/2003 | Choi et al. |
| 6,740,910 B2 | 5/2004 | Roesner et al. |
| 6,830,981 B2 | 12/2004 | Lee et al. |
| 6,838,297 B2 | 1/2005 | Iwasaki et al. |
| 6,858,891 B2 | 2/2005 | Farnworth et al. |
| 6,933,222 B2 | 8/2005 | Dubin et al. |
| 6,979,590 B2 | 12/2005 | Rueckes et al. |
| 6,995,046 B2 | 2/2006 | Rueckes et al. |
| 7,045,421 B2 | 5/2006 | Rueckes et al. |
| 7,081,385 B2 | 7/2006 | Farnworth et al. |
| 7,091,096 B2 | 8/2006 | Balasubramanian et al. |
| 7,132,714 B2 | 11/2006 | Bae et al. |
| 7,135,773 B2 | 11/2006 | Furukawa et al. |
| 7,211,844 B2 | 5/2007 | Furukawa et al. |
| 7,652,418 B2 | 1/2010 | Choi et al. |
| 7,736,979 B2 * | 6/2010 | Farrow et al. ................. 438/270 |
| 7,964,143 B2 | 6/2011 | Farrow et al. |
| 2003/0102222 A1 | 6/2003 | Zhou et al. |
| 2005/0095466 A1 | 5/2005 | Minteer et al. |
| 2005/0118494 A1 | 6/2005 | Choi |

(Continued)

FOREIGN PATENT DOCUMENTS

JP       2001312953      11/2001

(Continued)

OTHER PUBLICATIONS

W. B. Choi et al., Electrophoresis Deposition of Carbon Nanotubes for Triode-Type Field Emission Display, 78 Appl. Phys. Lett. 1547-1549 (2001).*

(Continued)

*Primary Examiner* — Prem C Singh
*Assistant Examiner* — Randy Boyer
(74) *Attorney, Agent, or Firm* — McCarter & English, LLP

(57) ABSTRACT

A nanotube device and a method of depositing nanotubes for device fabrication are disclosed. The method relates to electrophoretic deposition of nanotubes, and allows a control of the number of deposited nanotubes and positioning within a defined region.

20 Claims, 10 Drawing Sheets

U.S. PATENT DOCUMENTS

| | | | |
|---|---|---|---|
| 2005/0156203 | A1 | 7/2005 | Bae et al. |
| 2005/0167655 | A1 | 8/2005 | Furukawa et al. |
| 2006/0169972 | A1 | 8/2006 | Furukawa et al. |
| 2006/0233694 | A1 | 10/2006 | Sandhu et al. |
| 2006/0249388 | A1 | 11/2006 | Chang et al. |
| 2006/0286023 | A1 | 12/2006 | Huang |
| 2007/0287034 | A1 | 12/2007 | Minter et al. |

FOREIGN PATENT DOCUMENTS

| | | |
|---|---|---|
| JP | 2006111498 | 4/2006 |
| WO | WO 03/081687 | 10/2003 |

OTHER PUBLICATIONS

Y. Nakayama and S. Akita, Field-Emission Device with Carbon Nanotubes for a Flat Panel Display, 117 Synth. Met. 207-210 (2001).*

A. R. Boccaccini et al., Electrophoretic Deposition of Carbon Nanotubes, 44 Carbon 3149-3160 (2006).*

H. Kim et al., Parallel Patterning of Nanoparticles via Electrodynamic Focusing of Charged Aerosols, 1 Nature 117-121 (2006).*

Choi et al., Electrophoresis Deposition o fCarbon Nanotubes for Triode-Type Field Emission Display, 78 Appl. Phys. Lett. 1547-1549 (2001).

Choi et al., Ultrahigh-Density Nanotransistors by Using Selectively Grown Vertical Carbon Nanotubes, 79 Appl. Phys. Lett. 3696-3698 (2001).

Lin et al., Glucose Biosensors Based on Carbon Nanotube Nanoelectrode Ensembles, 4 Nano Lett. 191-195 (2004).

Kim et al, Parallel Patterning of Nanoparticles via Electrodynamic Focusing of Charged Aerosols, 1 Nature Nanotechnology, 117-121-(2006).

Choi et al., Carbon Nanotube for Nanoelectronics, IEEE-NANO 2003, San Francisco, CA 2003.

Yamoto et al., Orientatioin and Purification of Carbon Nanotubes Using AC Electrophoresis, J. Phys. D: Appl. Phys. 31 (1998), pp. L34-L36.

Choi et al., Electrophoresis Deposition of Carbon Nanotubes for Triode-Type Field Emission Display, Applied Physics Letters, vol. 78, No. 11, Mar. 12, 2001, pp. 1547-1549.

Duesberg et al., Growth of Isolated Carbon Nanotubes with Lithographically Defined Diameter and Location, Nano Letters, 2003, vol. 3, No. 2, pp. 257-259.

Hoenlein et al., Carbon Nanotubes for Microelectronics: Status and Future Prospects, Materials Science and Engineering C23 (2003), pp. 663-669.

Duesberg et al., Ways Towards the Scalable Integration of Carbon Nanotubes into Silicon Based Technology, Diamond and Related Materials 13 (2004), pp. 354-361.

Graham et al., Towards the Integration of Carbon Nanotubes in Microelectronics, Diamond and Related Materials 13 (2004), 1296-1300.

Hahn et al., Fabrication of Clean Carbon Nanotube Field Emitiers, Applied Physics Letters 88, 113101, (2006).

Kim et al., Parallel Patterning of Nanoparticles via Electrodynamic Focusing of Charged Aerosols, Nature Nanotechnology, vol. 1, No. 2006, pp. 117-121.

Choi, Ultrhigh-Density Nanotransistors by Using Selectively Grown Vertical Carbon Nanotubes, Applied Physics Letters, vol. 70, No. 22, Nov. 26, 2001, pp. 3696-3698.

Bae, et al., Field Emission Properties of Carbon Nanotubes Deposited by Electrophoresis, Physica B 323 (2002), pp. 168-170.

Ma, et al., Electron Field Emission Properties of Carbon Nanotubes-Deposited Flexible Film, Applied Surface Science 251 (2005), pp. 258-261.

Kurnosov et al., Influence of the Interelectrode Distance in Electrophoretic Cold Cathode Fabrication on the Emission Uniformity, Applied Surface Science 215 (2003), pp. 232-236.

PCT Notification of Transmittal of the International Search Report and the Written Opinion o fthe International Search Authority, mailed Feb. 10, 2009 (8 pages).

Catrysse et al., RTO Technical Report 59: Electromagnetic Compatibility in the Defense Systems of Future Years, NATO, Jun. 2002, pp. 3-54.

Merkulov et al., Alignment Mechanism of Carbon Nanofibers Produced by Plasma-Enhanced Chemical-Vapor Deposition, Applied Physics Letters, vol. 79, No. 18, Oct. 29, 2001, pp. 2970-2972.

Katz et al., A Non-Compartmentalized Glucose $O_2$ Biofuel Cell by Bioengineered Electrode Surfaces, Journal of Electroanalytical Chemistry, vol. 479 (1999), pp. 64-68.

Cai et al., Direct Electron Transfer of Glucose Oxidase Promoted by Carbon Nanotubes, Analytical Biochemistry, vol. 332, (2004), pp. 75-83.

* cited by examiner

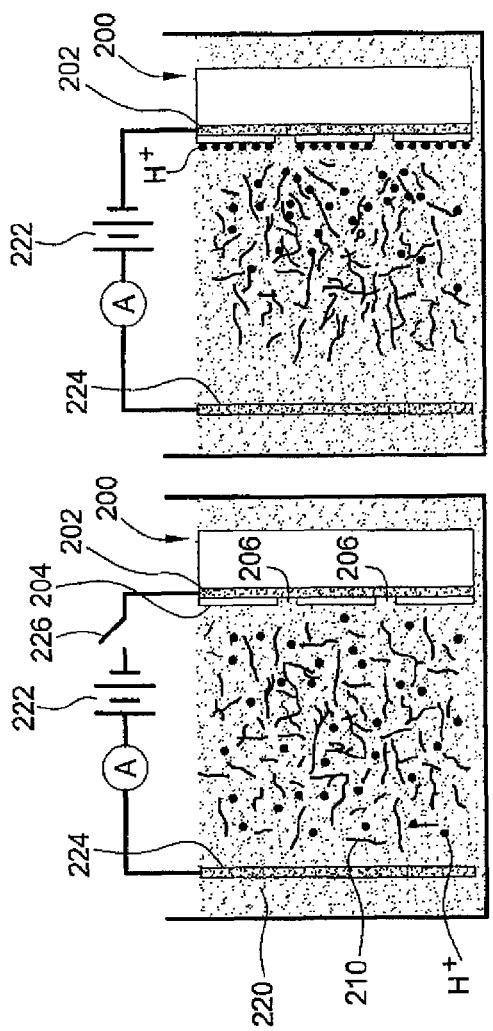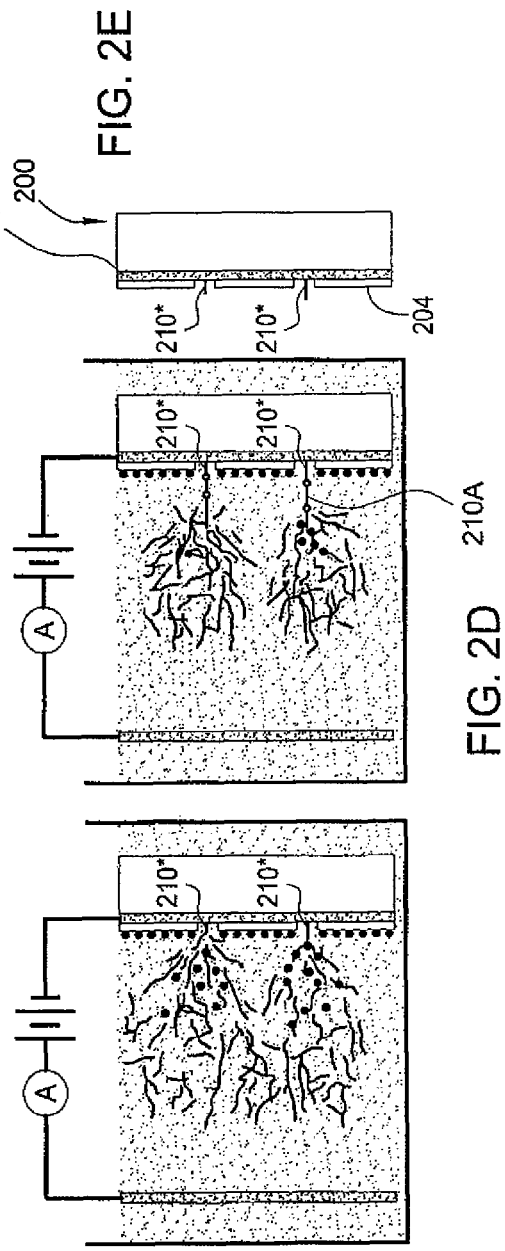

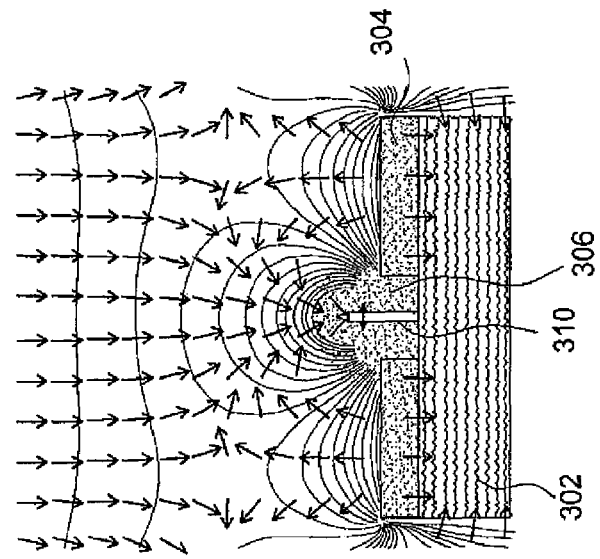
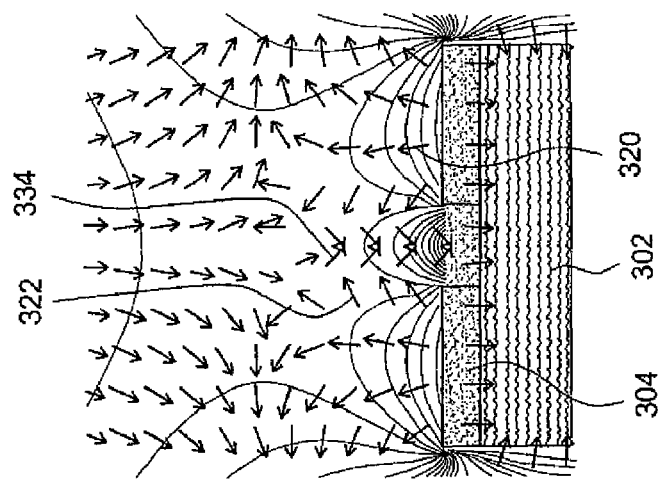
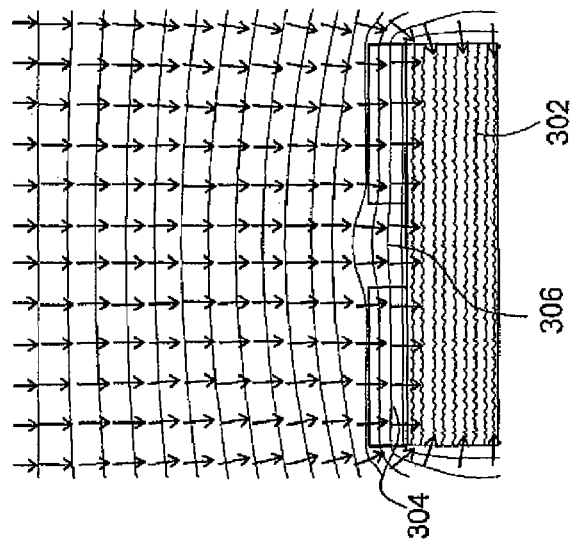

NANOTUBE DEVICE AND METHOD OF FABRICATION

CROSS REFERENCE TO RELATED APPLICATIONS

This application is a divisional patent application that claims priority benefit to a co-pending, commonly assigned non-provisional patent application entitled "Nanotube Device and Method of Fabrication," which was filed on Jun. 20, 2007, and assigned Ser. No. 11/765,735, the entire contents of which are incorporated herein by reference. The noted non-provisional application contains subject matter related to commonly owned U.S. patent application Ser. No. 11/765,788, "Method of Forming Nanotube Vertical Field Effect Transistor," which was filed concurrently therewith, and which is herein incorporated by reference in its entirety.

STATEMENT OF GOVERNMENT RIGHTS

This invention was made with U.S. Government support under grant contract number AFOSR Grant: FA9550-05-1-0461 awarded by the Air Force Office of Scientific Research. The Government has certain rights in this invention.

FIELD OF THE INVENTION

The present invention generally relates to a nanotube device and method of forming the device, and more particularly, to a method for controllably depositing one or more nanotubes in a defined region.

BACKGROUND OF THE INVENTION

There are many applications where a nanotube, e.g., a carbon nanotube (CNT), or an array of nanotubes, can be employed as a sensing or active device element in an electrical probe or electronic device. In these applications, electrical contact must be made with the nanotube, which requires accurate positioning of the nanotube with respect to various conductive links (i.e. interconnects) and other circuitry.

Aside from the need for precise alignment, properties of the nanotube also need to be controlled in order to provide device performance according to desired specifications. For example, many transistor applications for CNTs are best achieved with single wall carbon nanotubes (SWNT) rather than multi-wall carbon nanotubes (MWNT). Furthermore, as an active element of a transistor, a semiconducting SWNT, rather than a metallic SWNT, is required. For other applications such as interconnects and nanoprobes, however, a metallic CNT is preferred.

Existing fabrication methods for CNT devices do not fully address both needs for alignment and property control. In addition, in CNT electrical device fabrication, at least one interconnect level may be processed before CNT deposition. The most common metallization schemes, e.g., with aluminum and copper interconnects, often impose thermal budget constraints for subsequent processing steps. Chemical vapor deposition (CVD) methods, which are typically used for depositing CNTs, are not compatible with aluminum or copper interconnects because of the relatively high temperatures involved.

SUMMARY OF THE INVENTION

Embodiments of the present invention provide a nanotube device and a method of depositing nanotubes for device fabrication.

One embodiment relates to a method that includes: (a) defining a region on a structure by an aperture, (b) configuring the aperture to control a number of nanotubes to be deposited by electrophoresis in the region, and (c) depositing the number of nanotubes in the region by electrophoresis.

Another embodiment of the invention provides a nanotube-based sensor, that includes an insulating layer over a metal contact formed on a substrate, an aperture formed in the insulating layer, the aperture extending to the metal contact and defining a region at the metal contact, a carbon nanotube disposed inside the aperture and having a first end contacting the region at substantially a center of the region, and a second end coupled to a molecule having a functional group for interacting with a sample.

Yet another embodiment provides a method of forming a carbon nanotube-based device, the method includes providing a substrate with an insulating layer formed on a metal contact, forming an aperture through the insulating layer to expose a region of the metal layer, immersing the substrate in an electrolytic fluid containing carbon nanotubes, providing a metal electrode in the electrolytic fluid, applying a bias voltage across the metal contact and the metal electrode, and depositing at least one carbon nanotube in a substantially perpendicular orientation with respect to the region, in which one end of the carbon nanotube contacts the region proximate a center of the region.

BRIEF DESCRIPTION OF THE DRAWINGS

The teachings of the present invention can be readily understood by considering the following detailed description in conjunction with the accompanying drawings, in which:

FIGS. 2A-E are schematic diagrams illustrating an experimental setup and a process sequence for depositing a carbon nanotube according to one embodiment of the present invention;

FIGS. 3 A-C are schematic illustrations of the electric field distributions around an aperture with a diameter of 100 nm and a depth of 50 nm;

To facilitate understanding, identical reference numerals have been used, where possible, to designate identical elements that are common to the figures.

DETAILED DESCRIPTION

In the fabrication of CNT devices, there is often a need to provide a vertically oriented CNT inside an aperture. In transistor fabrication processes, depending on the specific stage or levels, the aperture is also referred to as a via.

Embodiments of the present invention provide a method of depositing nanotubes in a region defined by an aperture, with control over the number of nanotubes to be deposited, as well as the pattern and spacing of nanotubes. Specifically, electrophoretic deposition, along with proper configuration of the aperture, allows at least one nanotube to be deposited in a target region with nanometer scale precision. Pre-sorting of nanotubes, e.g., according to their geometries or other properties, may be used in conjunction with embodiments of the invention to facilitate fabrication of devices with specific performance requirements.

Figure 1:
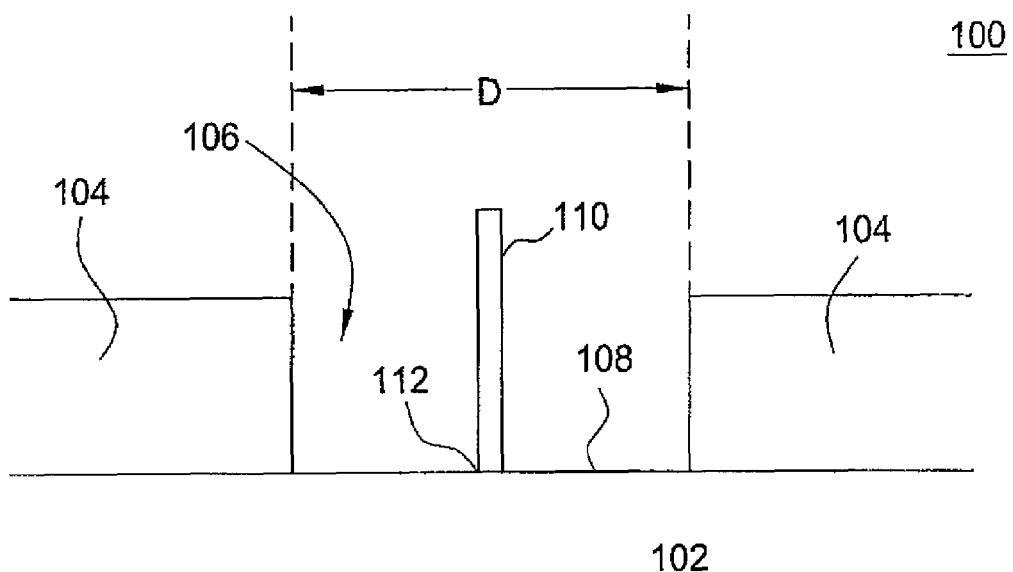
FIG. 1 is schematic cross-sectional view of a nanotube-based structure that can be fabricated using embodiments of the present invention.

FIG. 1A is a schematic cross-sectional view of a nanotube structure 100 that can be fabricated using embodiments of the present invention. The structure 100 includes a substrate 102, over which an insulating material layer 104 has been deposited. The insulating layer 104 has been patterned to form an aperture 106, which exposes a top surface 108 of the substrate 102. A single CNT 110 is deposited inside the aperture 106 so that one end 112 of the CNT 110 contacts the top surface of the substrate 102. The substrate 102 is a conducting material such as a metal or a conducting film (deposited over an insulating material) that allows a bias voltage to be applied for electrophoretic deposition of the nanotube 110.

Embodiments of the present invention allow the CNT 110 to be deposited inside the aperture 106, to the exclusion of other CNTs. The aperture 106, which has to be sufficiently large to accommodate the CNT 110, may be patterned using different lithographic processes. Thus, in one embodiment; the aperture 106 may have a diameter (D) ranging from about the lower limit (e.g., resolution) of the lithography process to about 100 nm. For example, existing lithography at 193 nm readily provides a resolution limit of about 90 nm. In one embodiment, the substrate 102 has a lateral dimension (e.g., extending across the aperture) sufficiently large to meet level-to-level overlay constraints with respect to the aperture 106. As will be shown below, the CNT 110 can be deposited proximate the center of the aperture 106, e.g., with a lateral alignment precision of a few nanometers. Furthermore, the CNT 110 may be pre-selected to have a preferred physical property including multiwall CNT versus single wall CNT and or conducting CNT versus semiconducting CNT.

FIGS. 2A-D illustrate schematically an experimental setup for electrophoresis and a sequence for depositing a CNT on a substrate according to one embodiment of the present invention. Electrophoretic deposition (EPD) is driven by the motion of charged particles, dispersed in a suitable solvent, towards an electrode under the influence of an electric field. Particles less than about 30 μm size can be used in suspensions with low solid loading and low viscosity. In general, whether nanotubes are deposited in the form of bundles or individual tubes depends on the nature of the suspension and the relative mobilities of each, which depends on their shapes and the associated resistance to diffuse towards the contact surface inside the apertures or vias.

FIG. 2A shows a substrate structure 200 with a conductive layer 202. An insulating layer 204 is provided over the conductive layer 202, and one or more apertures 206 are patterned in the insulating layer 204. The substrate structure 200 is immersed in a liquid bath 220, e.g., at room temperature, containing an electrolyte and a suspension of CNTs 210 in a suitable solvent.

Successful EPD requires preparation of a stable dispersion. In general, an electrostatically stabilized dispersion can be obtained with particles of high ζ-potential, while keeping the ionic conductivity of the suspensions low. SWNTs have shown high ζ-potential values at low pH values. It is also known that the presence of charging salts can play an important role in improving adhesion of the nanotubes to substrates and increasing the deposition rates.

In one embodiment, 10 mg of purified SWNTs are suspended in 30 ml of distilled water, and $10^{-4}$ moles of magnesium nitrate hexahydrate [Mg(NO$_3$)26H$_2$0] is added to the suspension and sonicated for about 2-3 hrs. In general, it is preferable that the nanotubes in the liquid bath 220 be pre-sorted for the type of nanotubes according to application needs. For example, while semiconducting SWNTs are used as active elements in transistors, either semiconducting or metallic nanotubes may be used for probes or other devices. A few drops of non-ionic Triton-X surfactant are added to improve the suspension with a final pH of solution at about 4.

Aside from hydrogen ions ($H^+$), shown as circles in FIG. 2A, the liquid bath 220 also contains magnesium ions, $Mg^{2+}$, which tend to adsorb or attach to the CNTs. An electrode 224, e.g., a platinum electrode, is immersed in the liquid bath 220 and connected to a positive terminal of a DC voltage source 222. The conducting layer 202 is connected to a switch 226.

In FIG. 2A, when the switch 226 is open and there is no current flow inside the liquid bath 220 (current flow may be measured using an ammeter A), the CNTs are randomly distributed in the suspension and any deposition on the substrate will be random.

In FIG. 2B, the switch 226 is closed, thus connecting the conductive layer 202 to a negative terminal of the DC source 222. With a DC potential, e.g., in a range of about 5V-25V, applied across the platinum electrode 224 and the conductive layer 202, charged particles or species in the fluid will move towards either the cathode or the anode. For example, $H^+$ ions and positively charged CNTs will move towards the substrate structure 200, which is the cathode in this case.

Since $H^+$ ions have higher mobility than other positively charged species, including the CNTs, $H^+$ ions will arrive at the substrate structure 200 faster than other charged species, and thus, preferentially accumulate on the surface of the insulating layer 204, as shown in FIG. 2B. The positively charged surfaces of the insulating layer 204 result in an electric field being produced around each aperture 206.

Positively-charged CNTs arriving near the substrate structure 200 are directed by the electric field towards the center of each aperture 206, as shown in FIG. 2C. Details regarding this "focusing" effect will be presented in later discussions. In one embodiment, the apertures 206 and electric field distribution are configured so that only one CNT (shown as CNT 210*) is deposited inside each aperture 206, even though the diameter (or lateral dimension) of the aperture 206 is large enough to physically accommodate additional CNTs. The CNT 210* is disposed inside each aperture 206 in a "longitudinal" manner, i.e., the length of the CNT 210* is along the same direction as the depth of the aperture 206, with one end of the CNT contacting the conductive layer 202.

FIG. 2D shows that the unattached end of CNT 210* tends to align or point towards the platinum electrode, and further, serves as a focal point for additional CNTs. Thus, a second CNT 210A becomes attached to the free end of CNT 210*, e.g., in a lengthwise manner, with additional CNTs attaching to each other end-to-end. The substrate structure 200 is then removed from the bath 220, washed in distilled and de-ionized water, and dried with an inert gas. After drying, only the CNTs 210* that are attached to the conductive layer 202 remain, and the resulting structure, such as one illustrated in FIG. 2E, is ready for further processing.

Since different devices often require different properties of the nanotubes for proper operation and/or optimum performance, it may be advantageous to provide a presorting of the nanotubes prior to electrophoretic deposition. For example, nanotubes may be sorted according to their properties such as semiconducting versus metallic, single-walled versus multi-walled, or they may be sorted according to geometries or dimensions such as lengths, diameters, and so on.

Since different types of nanotubes have different mobilities, e.g., longer or multiwalled nanotubes will generally have lower mobility compared to shorter or single-walled nanotubes, electrophoresis may also be used for sorting purposes. Such sorting can be done prior to the electrophoretic deposition so that the nanotubes in the bath have a relatively uniform distribution in terms of properties and/or geometries. Alternatively, if the nanotubes in the electrophoresis bath have a relatively wide distribution in terms of geometries or other properties, a certain degree of sorting may also be achieved "in situ" during deposition by virtue of the different mobilities of the nanotubes.

The degree of focusing that directs the nanotubes towards the aperture is affected by the magnitude and shape of the electric field distribution, along with the configuration of the aperture. To provide control over the number of deposited nanotubes as well as their positioning, a finite element model is used to investigate the electric field distribution as a function of various input parameters. Parameters or factors that are relevant for controlling nanotube deposition include the aperture configuration, nanotube properties, characteristics of the insulating layer and substrate, bias potential, dielectric properties of the solution, among others. The aperture configuration may generally include the shape, dimensions (e.g., width, length, depth, ratios of dimensions), sidewall profile, and so on. The nanotube properties may generally include the dimensions (e.g., length, diameter), single-walled or multi-walled, semiconducting or metallic.

The electric field around the aperture results from a combination of the potential applied to the metal layer on the substrate structure and charges that accumulate on the surface of the insulating layer. The positive charge accumulation on the dielectric layer covering the cathode creates an electric field that opposes the field arising from the bias applied between the anode and cathode. Once the two electric fields become equal and opposite, positive charges will no longer be attracted to the surface of the insulating layer. This "saturation charge density", $\sigma$, which determines the strength of the nanoscopic lens from the resulting electric field distribution, can be calculated from:

$$\sigma = \epsilon_0 \epsilon_r E \qquad \text{Eq. (1)}$$

where E is the magnitude of the electric field between the anode and cathode, $\epsilon_0$ is the permittivity of free space, and $\epsilon_r$ is the relative permittivity of the liquid.

As an example, for $E=10^3$ V/m, $\epsilon_0=8.85\times10^{-12}$ Farad/meter and the liquid is water $\epsilon_r=80$, the surface charge density $\sigma$ is equal to $7.1\times10^{-7}$ Coulomb/meter$^2$.

Once the specific aperture geometry is selected and the surface charge density is calculated, the electric field in the region near the apertures and the motion of positively charged particles can be calculated using finite element analysis techniques that are well known. Thus, with proper configuration and design, one can obtain an electric field distribution to produce a desired focusing or lens effect to direct the nanotube deposition.

FIGS. 3A-C show the results of electric field distributions around an aperture 306 having a diameter of 100 nm and a depth of 50 nm. In this example, a negative 10V bias is applied to the conductive layer 302. FIG. 3A shows the electric field distribution before H$^+$ ions are accumulated on the insulating surface. The electric field distribution is relatively uniform, with field lines mostly perpendicular to the surfaces of the insulating layer 304. As shown in the figure, the field line directions are indicated by arrows pointing towards a region of negative potential. Only slight deviations of the field lines are seen at or close to the aperture 306.

FIG. 3B shows the modified electric field distribution after the surface of the insulating layer 304 is saturated with H$^+$ ions. The arrows 320 above the insulating layer 304 show that positively charged species will be repelled away from the surface, while arrows 322 on either side of the aperture 306 show that the field lines are directed inwards, i.e., towards an area above the aperture 306. Near the center of the aperture 306, the field lines are directed downwards, i.e., towards the interior of the aperture 306, as indicated by arrows 334. Thus, positively charged species such as CNTs are directed towards the aperture 306.

After sufficient charges have accumulated to reach the charge saturation point, the electrostatic lens effect will direct all charged particles towards the center of the aperture 306. The equipotential lines for this geometry favor the focusing of mobile charged nanotubes towards the center of the aperture 306. In this case, the diameter of the aperture 306 is 100 nm and the depth is 50 nm. In this example, since the electric field distribution around the aperture 306 is substantially symmetric with respect to a central longitudinal axis of the aperture, the CNT 310 is also substantially centered inside the aperture 306. Thus, one end of the CNT 310 is attached to a region of the conductive layer 302 defined by the aperture 306 (i.e., the exposed region at the bottom of the aperture), e.g., within a few nanometers of the center of the defined region.

FIG. 3C shows the electric field distribution after one CNT 310 has been deposited inside the aperture 306. Since the CNT is conductive and is in electrical contact with the conductive layer 302, the electric field distribution is modified by the deposited CNT 310. Furthermore, if the aperture 306 is sufficiently small, as it is in this case, the electric field lines tend to concentrate towards the free end of CNT 310, instead of directing towards the interior of the aperture 306. Thus, the free end of CNT 310 becomes a focal point for further deposition of nanotubes, instead of being deposited at the bottom of the aperture 306.

In general, for a fixed potential difference between the reference electrode and the metal contact at the bottom of the aperture, the strength of the focusing effect is inversely proportional to the diameter of the aperture for a fixed aperture depth.

Figure 4A:
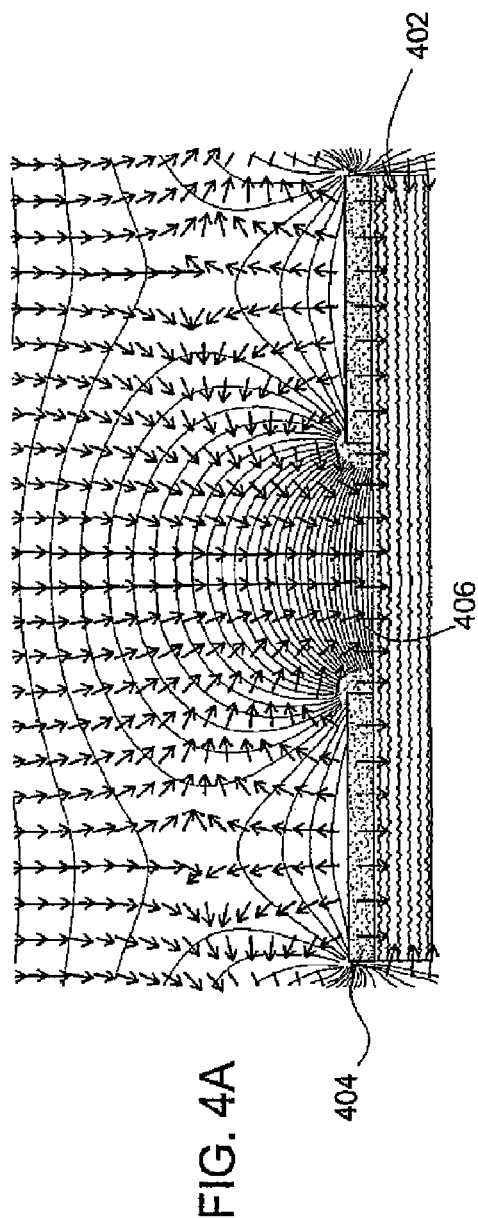
FIGS. 4A-B are schematic illustrations of electric field distributions around an aperture with a diameter of 500 nm and a depth of 50 nm.
Figure 4B:
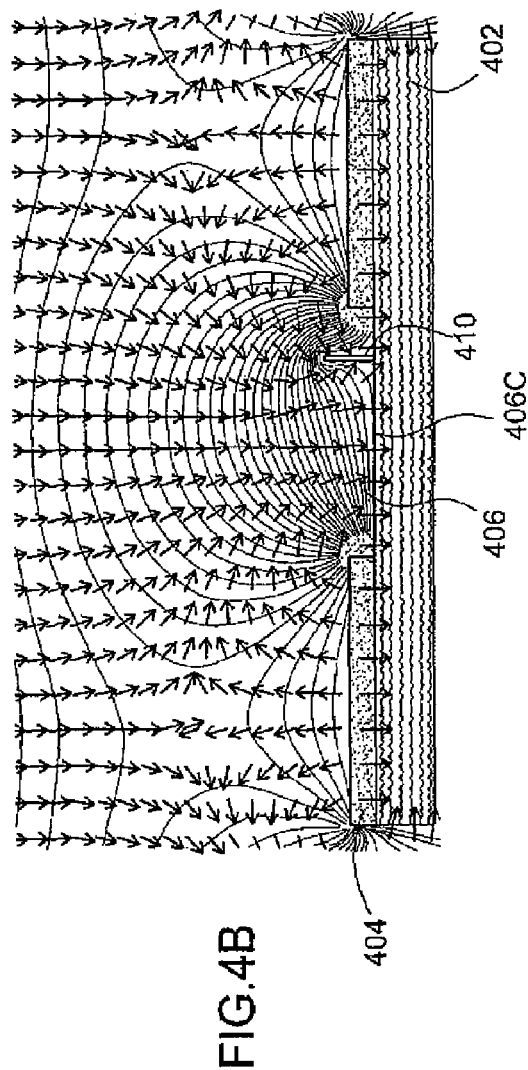

FIG. 4A-B show different results obtained for an aperture 406 having a diameter of 500 nm and a depth of 50 nm, with a negative 10V bias applied to a conductive layer 402. FIG. 4A shows the electric field lines around aperture 406, with H$^+$ ions accumulated on the surface of insulating layer 404, and FIG. 4B shows the electric field lines modified by a CNT 410 inside the aperture 406. In this case, the CNT 410 is positioned with a lateral offset from the center 406C of the aperture 406, which may arise, for example, from a random direction of approach in the bath, followed by the electric field directing the nanotube to its location of deposition. As suggested by the field lines in the figure, more than one CNT may be deposited inside the aperture 406.

In this case, the electric field distribution will not provide a preferential direction to guide the nanotubes towards the center region of the aperture 406. The final location of the nanotube will depend on the initial position of the nanotube before the bias is applied. For a large aperture, e.g., diameter or lateral dimension of greater than about 100 nm, the unattached end of the first deposited nanotube may still be the focal point for further nanotube deposition. However, when the lateral dimension of the aperture is sufficiently large, the electric field will also direct other nanotubes to other locations on the exposed surface of the conductive layer 402.

Although results suggest that an aperture diameter of about 100 nm provide a transition or reference point below which deposition is restricted to a single nanotube, while apertures larger than about 100 nm tend to favor deposition of more than one nanotubes, it is understood that this reference point may vary with specific combinations of nanotubes and/or structural configurations.

Aside from the aperture diameter (or lateral dimension), other parameters, e.g., shape, aspect ratio (defined as depth or height of aperture divided by lateral dimension), among others, may also be used for the purpose of controlling deposition of nanotubes, for example, by providing different configurations according to the nanotube properties and/or geometries.

Results of another finite element analysis also show that, for nanotubes with a 10 nm diameter and a length of 100 nm, and an aperture formed in silicon nitride with a diameter of 100 nm and a depth (or height) of larger than 18 nm, only one nanotube will be deposited inside the aperture. This suggests that an aperture with an aspect ratio of at least 0.18 or greater may be used to restrict the number of deposited nanotubes to only one. For a nanotube with a smaller diameter, a larger aspect ratio may be required in order to restrict the deposition to only one nanotube. Similar analysis can be used to simulate probable locations of deposited nanotubes for other aperture configurations and nanotube properties. While a two dimensional analysis is suitable for situations in which a plane of symmetry is available, a three dimensional analysis can generally be used for other situations. Thus, finite element analysis can be used for nanoscopic lens design as a guide to providing nanotube deposition with additional levels of control.

Many different nanotube-based devices may be fabricated using the method of the present invention. While the method can generally be applied to the deposition of nanotubes within apertures of different dimensions, it is particularly well-suited for situations in which it is desirable to control the number of nanotubes to be deposited or the lateral positioning or alignment of the nanotube. Examples of nanotube-based devices that can benefit from this method include vertical CNT transistors, chemical sensors or biosensors, among others.

Figure 5A:
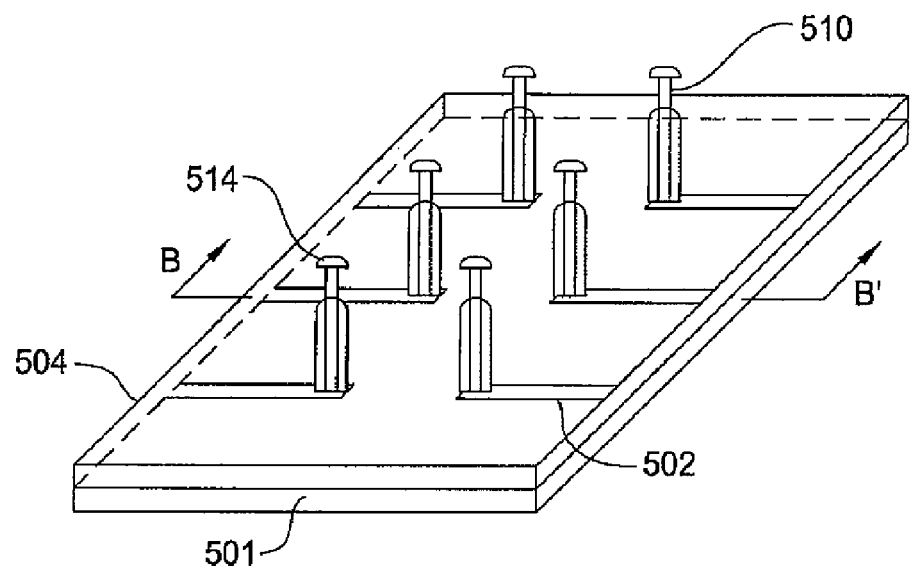
FIG. 5A is a schematic illustration of a nanotube sensor array.
Figure 5B:
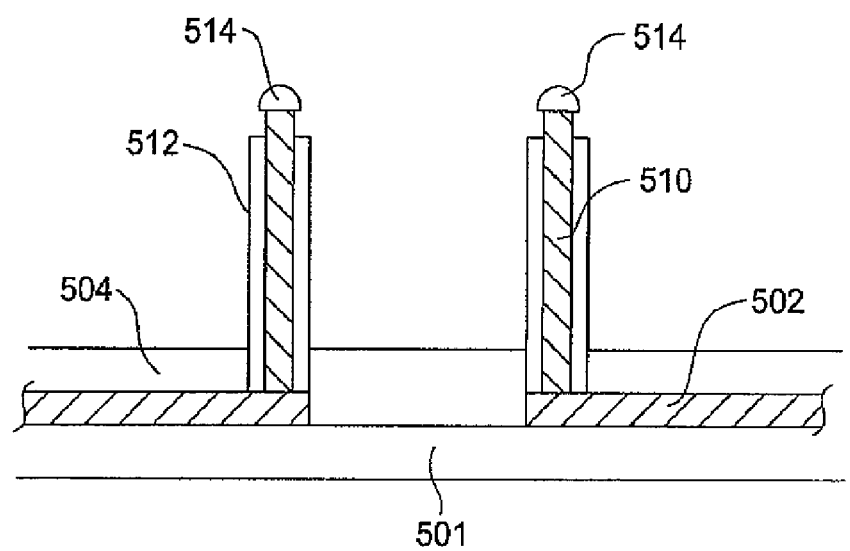
FIG. 5B is a cross-sectional view of the nanotube sensor array of FIG. 5A.

FIG. 5A is a schematic illustration of a nanotube-based sensor array device 500 according to one embodiment of the present invention, and FIG. 5B is a cross-sectional view along a vertical plane containing line BB'. Device 500 generally includes one or more nanotubes 510 that are deposited over a substrate 501. A conductive material 502, e.g., a metal, is formed at selected regions of the substrate 501 to provide conductive paths to the nanotubes 510. Nanotubes 510 can be deposited onto the conductive material 502 using electrophoresis as previously described, e.g., by forming apertures in an insulating layer 504 provided over the conductive material 502, and applying a bias voltage to the conductive material 502. A sheath 512 is also formed around each nanotube 510 to provide passivation and insulation for the nanotube 510. By insulating the sidewalls of the nanotubes 510 and leaving only the tips exposed, potential background noise may be reduced, thus increasing the electrical sensitivity of the sensor. The interconnects to the nanotubes 510 are used for measuring changes in the CNT electrical characteristics.

A device similar to that shown in FIGS. 5A-B may be used for investigating intracellular activities in biological cells. Specifically, a CNT is a good candidate for such a probe because its small diameter (e.g., compared to cell membrane thickness) can minimize distortions to the cell that is being investigated with the probe.

Depending on the specific sensor applications, different functional molecules 514 are provided to the other end of the nanotube 510. In general, SWNTs are preferred for sensor applications, although there may be situations in which MWNTs may also be used.

Figure 6A:
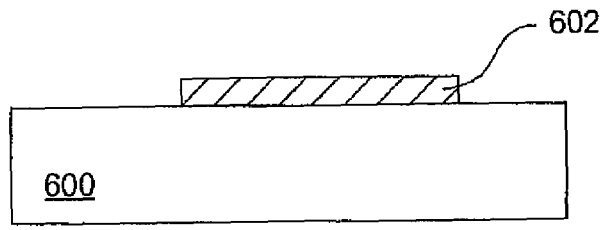
FIGS. 6A-J are illustrations of cross-sectional views of structures during various stages of a sensor fabrication sequence.

FIGS. 6A-J are schematic cross-sectional views of a sensor device structure during various stages of a process sequence suitable for forming a device array such as that shown in FIG. 5A. FIG. 6A shows a conductive portion 602 formed on a substrate 600. For a biosensor, quartz may be used as the substrate material, which will facilitate the viewing of a biological sample with an optical microscope in transmission mode. In one embodiment, quartz wafers of 100 mm diameter and 350 um thickness may be used, and they can be cleaned and prepared prior to device fabrication using methods known to one skilled in the art. In general, however, any suitable substrate will suffice, including silicon. If the starting substrate is silicon, or other conducting material, then an insulating layer will first have to be deposited prior to the metal interconnects.

The conductive portion 602, e.g., an interconnect metal, can be deposited and patterned using photolithography and resist liftoff techniques known to one skilled in the art. The interconnect metal needs to be suitable for maintaining electrical contact and adhesion with CNTs, and may include, but not limited to, cobalt (Co), nickel (Ni), or iron (Fe).

To facilitate adhesion between the metal interconnect to the quartz substrate, an adhesion layer (not shown) may also be formed prior to the formation of the conductive portion 602. In one embodiment, cobalt (Co) is used as a metal interconnect, and a 20 nm thick chromium (Cr) adhesion layer is used to promote adhesion of cobalt to the quartz surface. The Cr layer may be evaporated at a rate of about 2 Ångstroms per second (Å/s), and a 120 nm thick Co layer can then be evaporated at a rate of about 1 Å/s. A thickness of about 20 nm and 120 nm may be used for the Cr and Co layers, respectively. The cobalt metal interconnect can also serve as the cathode during electrophoretic deposition of the nanotube In the embodiment where CNTs are deposited using electrophoresis, the conductive portion 602 is configured to be electrically connected to contact pads (not shown) provided at the edge or periphery of the substrate 602. In one embodiment, each conductive portion 602 upon which a CNT will be deposited is provided as part of a continuous conductive layer formed over the substrate 600, in order to simplify the electrical connection paths. This facilitates electrical grounding of the metal during electron-beam lithography (if e-beam is used during fabrication) and provides a single connection point for electrophoretic deposition of CNTs. In one example, electrical connections between different devices are made in the kerf (area between each device), which allows the connections to be broken by a dicing saw when the substrate is cut to facilitate assembling the devices. Alternative configurations may also be used for providing the electrical connections needed during fabrication, and a variety of conventional lithographic and etching processes may be adapted for this purpose.

Figure 6B:
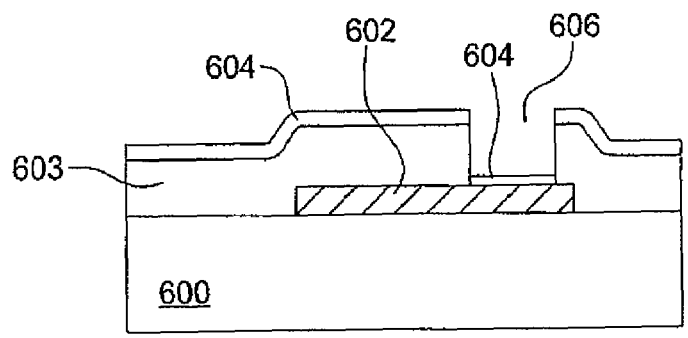
Figure 6C:
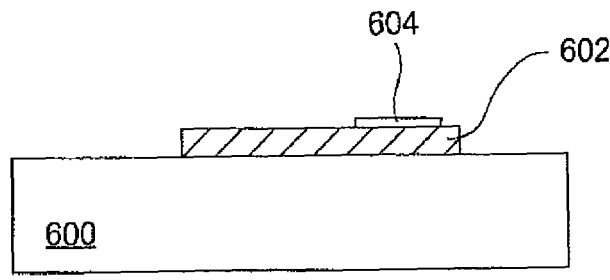

For each individual sensor device, a metal contact is needed to provide electrical connections to external circuits, for example, by soldering or wire bonding. In one embodiment, gold (Au) is used as the metal contact material. The metal contact can be formed using photolithography and resist liftoff techniques. FIG. 6B shows a structure during the metal contact formation stage, in which a photoresist layer 603 has been patterned to form an aperture 608 extending to an underlying region of the conductive portion 602. A conductive layer 604 is deposited over the patterned resist 603 and the exposed region of the conductive portion 602. When the resist layer 603 is removed from the structure of FIG. 6B, only the conductive layer inside the aperture 606 remains, resulting in a structure shown in FIG. 6C.

Figure 6D:
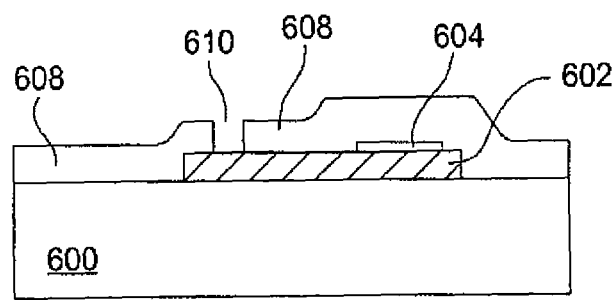

FIG. 6D shows an insulating layer 608 deposited over the substrate 600 and the conductive portion 602 and subsequently patterned to form an aperture 610 (also referred to as vias or windows). In one embodiment, silicon nitride (SiNx) is used as the insulating layer 608. The thickness of the insulating layer 608 is selected to provide an appropriate aspect ratio for electrostatic lens implementation after patterning. For example, a 50 nm thick SiNx film is suitable for forming apertures with a lateral dimension, e.g., diameter, of about 100 nm. For example, a 50 nm thick low stress SiNx film may be deposited at low temperatures by plasma enhanced chemical vapor deposition (PECVD) using Plasma Therm 790 standard equipment at a temperature of about 350° C. In the context of a sensor device, the SiNx layer serves two functions. Aside from providing an insulation layer for forming the apertures during device fabrication, the SiNx layer, in the completed sensor, also provides an insulating barrier between the conducting interconnect metal and the cell culture solutions in which measurements will be performed.

Using a suitable lithography process, aperture 610 having a lateral dimension of about 100 nm or less can be formed in the insulating layer 608. The aperture 610 is sufficiently large to accommodate a nanotube to be deposited onto substrate 602. In one embodiment, the aperture 610 has a diameter ranging from about the lower limit (e.g., resolution) of the lithography process to about 100 nm. In one embodiment, optical lithography using 193 nm source illumination may be used to pattern the aperture in photoresist, providing a resolution of about 90 nm. Alternatively, these apertures may also be fabricated using electron-beam lithography or a focused ion beam milling technique. Apertures with dimensions of less than about 100 nm are suitable for providing the electrostatic lens effect during electrophoretic deposition of nanotubes. The lithography technique of the interconnect metal and vias will limit the separation between the nanotube devices.

The structure of FIG. 6D can then be immersed in an electrolytic bath for electrophoretic deposition of nanotubes, using a similar setup as previously discussed in connection with FIG. 2. In one embodiment, a patterned structure with a cobalt metal layer on a quartz substrate is used as the negative electrode, and a platinum wire is used as the positive electrode. DC bias voltages in the range of about 5 V-25 V may be used.

Figure 6E:
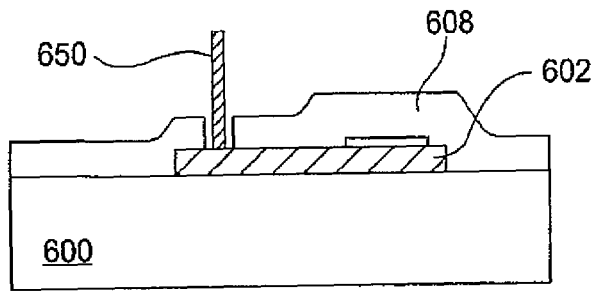
Figure 6F:
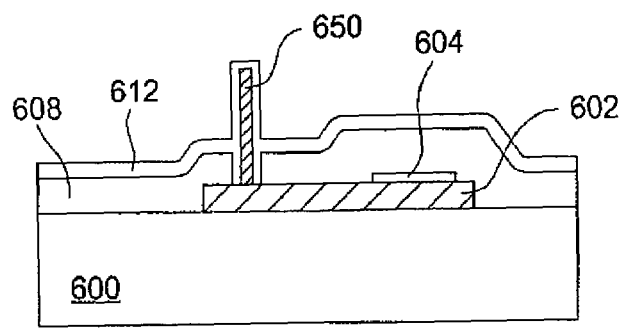

FIG. 6E shows a structure after deposition of a nanotube 650 inside the aperture 610. Prior to electrophoretic deposition, the nanotubes may be presorted for metallic SWNTs and filtered to limit bundles of SWNTs. The length of the CNTs or SWNTs may, for example, be less than about 1 micron (μm), and will typically be determined by the application needs. In the case of a biosensor such as an intracellular probe, the length may depend on requirements for mechanical stability and penetration distance into the target cell.

After the nanotube 650 is deposited in the aperture 610, its vertical orientation may be affected by the rinse process or by charging effects. The nanotubes can be realigned to the vertical direction by applying an electrical potential between the metal level on which it was deposited and a metal plate above the wafer substrate. This may be done, for example, in a reactor prior to the subsequent deposition process in the fabrication sequence. Plasma processing systems typically have a metal plate above the wafer that is part of the electrical circuit for generating the plasma. By establishing a DC or AC electric field between this metal plate (or another electrode) and the metal level that the nanotube is deposited on, the nanotube can be re-aligned to a desired orientation prior to subsequent processing.

After nanotube deposition, a conformal film 612 of an insulating material having a thickness range of about 2-5 nm may be formed to encapsulate and passivate (or insulate) the nanotube 650. Suitable materials for this encapsulation film include SiNx or suitable polymers, e.g., polytetrafluoroethylene.

Figure 6G:
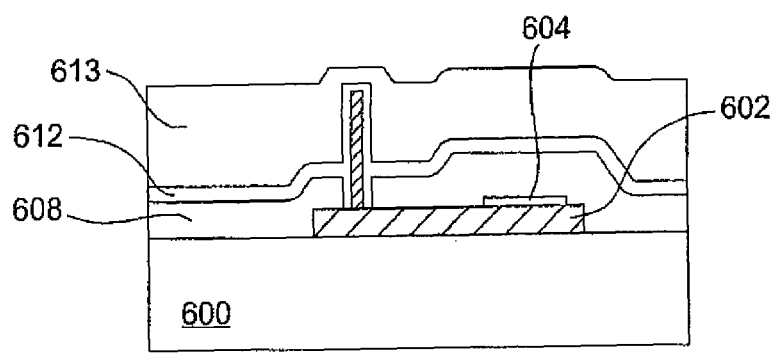
Figure 6H:
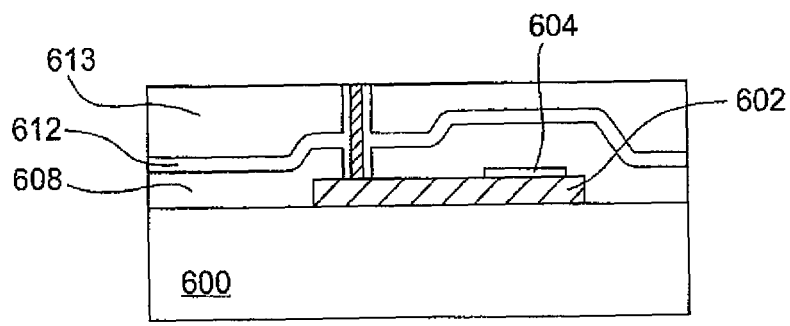

Since the sorting of nanotubes before or during electrophoretic deposition usually does not provide sufficiently precise control of the lengths of the nanotubes, additional trimming may be needed in order to provide a nanotube with a certain length specification. This can be achieved by the process steps illustrated in FIGS. 6G-H, showing a polysilicon layer 613 formed (e.g., grown or deposited) over the encapsulation film 612 (FIG. 6G). The polysilicon layer 615 can then be polished back, e.g., using chemical mechanical polishing (CMP), until the desired nanotube length is achieved, as shown in FIG. 6H.

A portion of the encapsulation film 612 around the tip of the deposited nanotube 650 can then be removed by a brief reactive ion etching (RIE) or chemical etch to uncover the tip of the nanotube 650. The length of nanotube 650 that is uncovered will depend on the etch rate and the time duration of the etch. RIE etches for SiNx are standard processes for fabrication of complementary metal oxide semiconductor (CMOS) integrated circuits, and etch rates are well known and incorporated into commercial SiNx etching apparatus.

Figure 6I:
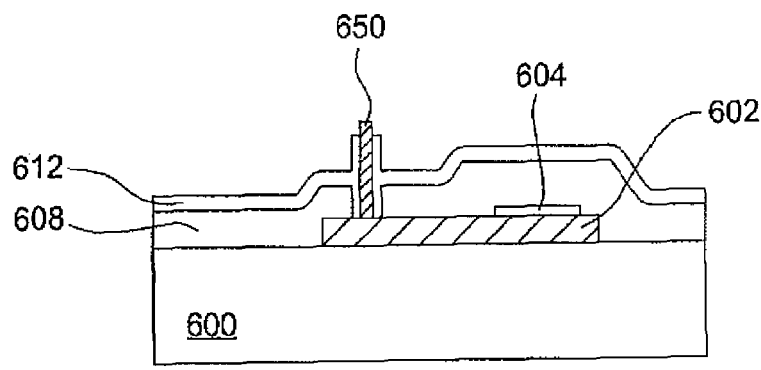
Figure 6J:
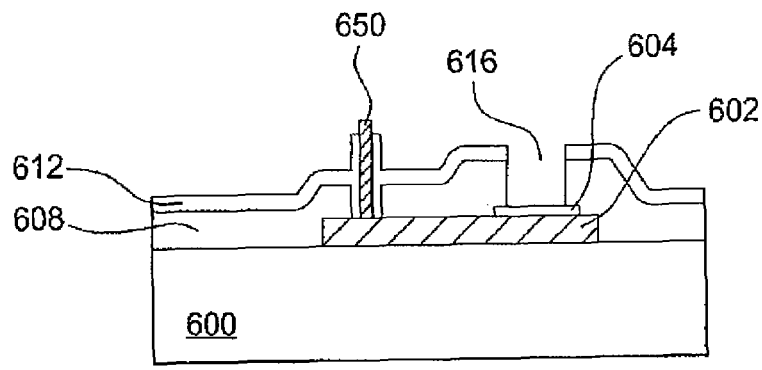

The poly-Si layer 613 will then be removed to leave free standing encapsulated nanotube 650, as shown in FIG. 6I. FIG. 6J shows the structure after an aperture 616 is formed in the encapsulation film 612 and insulating layer 608 to expose the metal contact 606. The aperture 616 can be formed with standard photolithography and dry etching process that are known to one skilled in the art.

Figure 7:
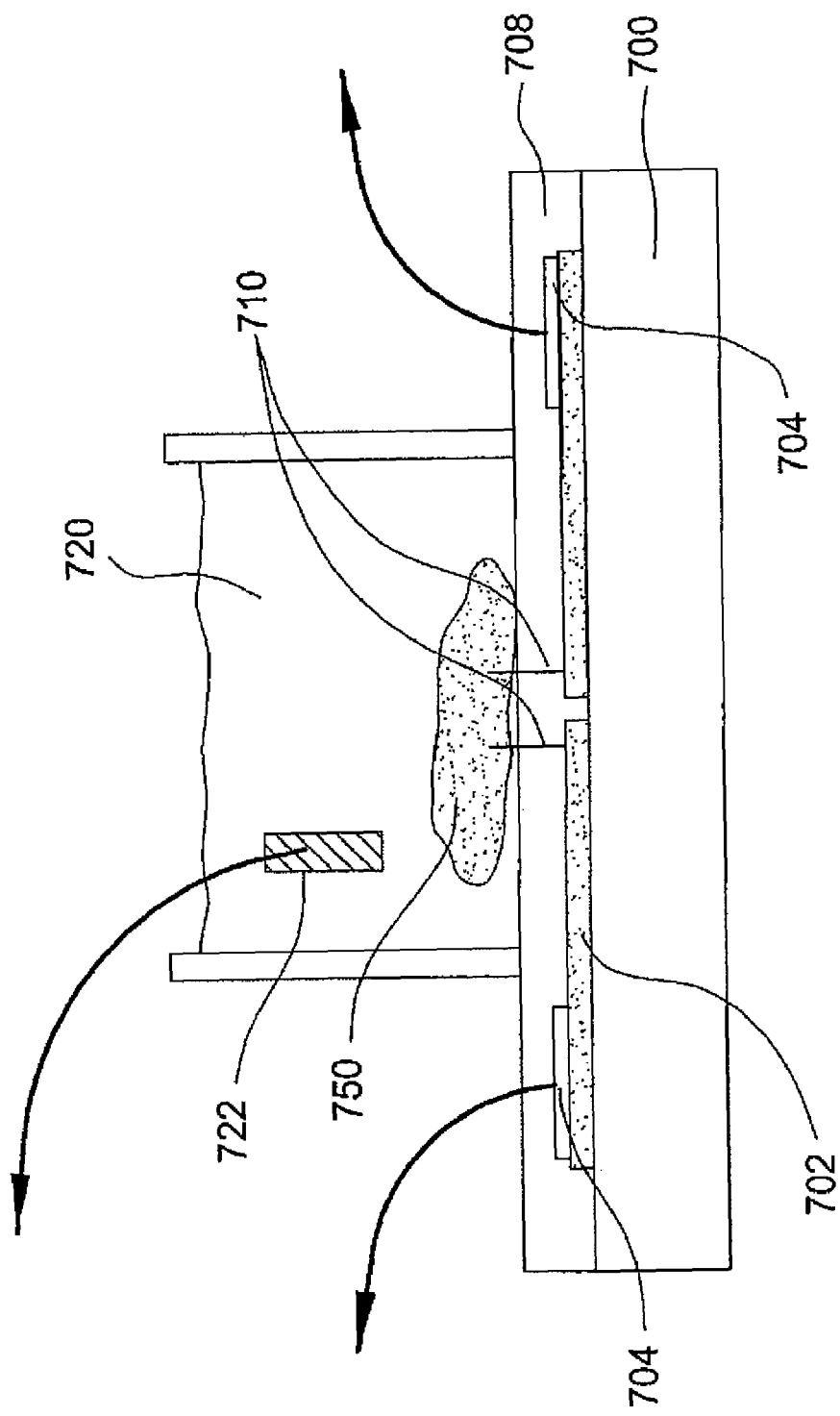
FIG. 7 is a schematic illustration of an experimental arrangement of using a nanotube sensor as an intracellular probe.

FIG. 7 is a schematic illustration of an experimental arrangement of using such a nanotube sensor as an intracellular probe. FIG. 7 shows two CNT probes 710, each connected to respective interconnect metal 702 formed over substrate 700. The CNT probes 710 are inserted into a cell 750 in a liquid bath 720 for electrical probing. A bath electrode 722 and the contact pads 704 (provided inside an aperture formed in insulating layer 708) are each connected to suitable electronics (not shown) to monitor the electrical characteristics indicative of intracellular activities.

The above embodiments and discussions illustrate the capability to controllably deposit a single nanotube with nanoscale lateral precision near a center of a region defined by an aperture. The method is particularly attractive from an implementation or processing viewpoint, because the ability to achieve such controlled deposition within a relatively large region significantly relaxes the requirement for lithographic techniques. As such, the fabrication can readily be performed using optical lithography, without resorting to more complicated lithographic tools (such as e-beam or focused ion beam) to form sufficiently small apertures to define the target deposition region.

Embodiments of the present invention also provide a method of controlling the number of nanotubes to be deposited and their spacings in a given region. Such a method is useful for many applications where it is desirable to deposit more than one nanotube in a defined region. For example, certain vertical field effect transistor (VFET) designs may benefit from having more than one nanotube forming a channel to allow more current to flow through the device. Thus, by controlling the number of nanotubes to be deposited, one can ensure that the VFET output can be designed with sufficient current to meet the parameters of a logic circuit input.

Figure 8:
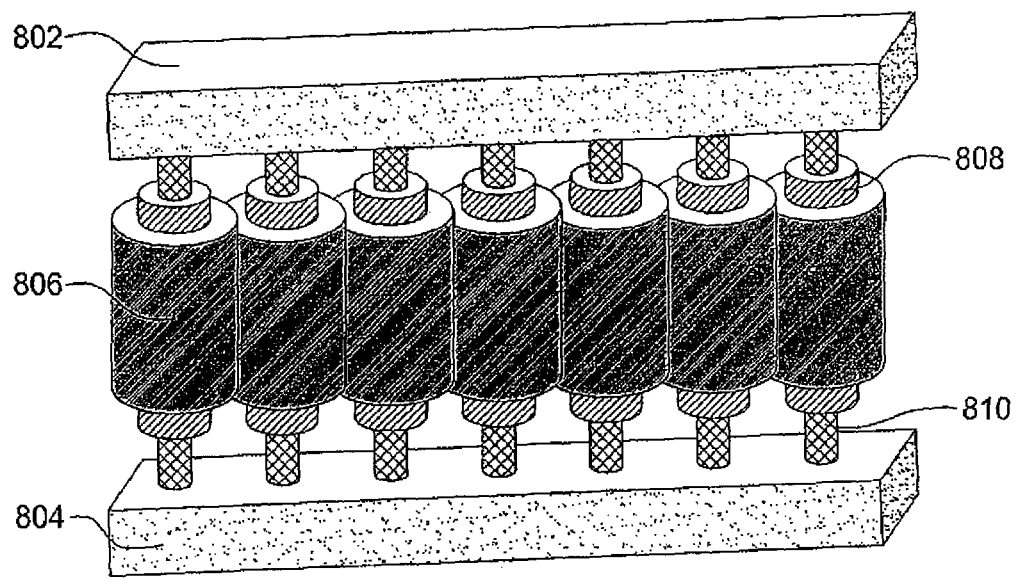
FIG. 8 is a schematic illustration of a nanotube-based transistor that can be fabricated using embodiments of the present invention.

One constraint in the design of the VFET is that the lateral size of the device should be as small as possible to maximize the number of VFETs per unit area. One possibility is to fabricate closely spaced vias and connect each source 802, drain 804, and gate 806 in parallel, as shown in FIG. 8 (with CNT 810 serving as the channel of the device and separated from the gate 806 by gate dielectric 808). This concept was suggested by Hoenlein et al., Materials Science and Engineering C, 23, p. 663-669 (2003); and DE 0010036897 C1, (2000). However, the difficulty with fabricating closely spaced vias for positioning nanotubes is that the number of nanotubes per unit area is solely determined by the minimum diameter of the vias and the separation between vias. This imposes a stringent requirement on lithography and etch processing and, for VFET devices with reasonable maximum current per unit length (1500 microampere per micrometer), sub-20 nm diameter vias will be required.

Embodiments of the present invention will allow a device concept such as that shown in FIG. 8 to be fabricated without imposing stringent requirements on lithography. Specifically, an aperture can be configured to control the number of nanotubes, as well as their spacing or positioning, within the apertured region using electrophoretic deposition.

Figure 9A:
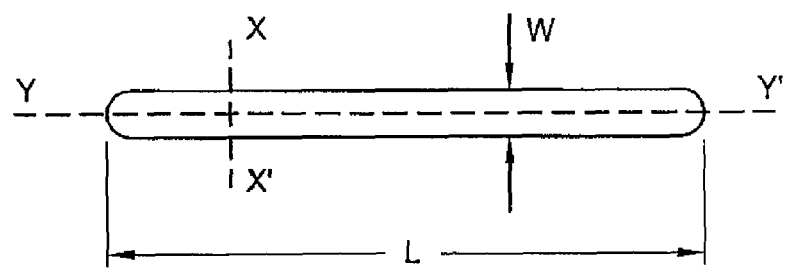
FIGS. 9A-B are schematic illustrations of a configuration of an aperture suitable for implementing embodiments of the present invention.
Figure 9B:
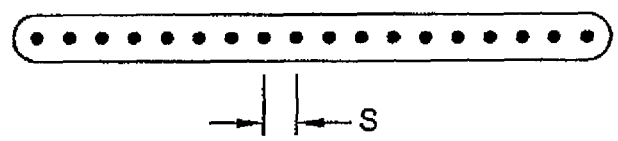

FIGS. 9A-B are schematic illustrations of a top view of an aperture configuration suitable for controlling nanotube deposition. As shown in FIG. 9A, the aperture has an elongated geometry such as a slot, which is characterized by a width (W), also referred to as a lateral or transverse dimension (along a direction indicated by line X-X'), and a length (L), also referred to as a longitudinal dimension (along a direction indicated by line Y-Y'), with L being larger than W. In this example, the width W is designed to be sufficiently narrow so as to allow only one nanotube to be deposited along the transverse direction. Thus, all deposited nanotubes will be deposited in a line pattern, i.e., lined up adjacent to each other, along the longitudinal direction.

Furthermore, the number of nanotubes deposited within the slot can be controlled by the length of the slot. Once a first nanotube is deposited in the slot, the electric field distribution around the slot will be modified. The new field distribution can be calculated using finite element analysis. The closest separation between adjacent nanotubes can also be calculated by using finite element analysis to predict the trajectory of randomly approaching charged particles that are successively deposited in the slot.

Using this analysis for nanotubes having a length of 100 nm, it has been estimated that the closest separation between nanotubes with 1 nm diameter is about 15 nm. For nanotubes with a diameter of 10 nm and a length of 100 nm, the closest separation for adjacent nanotubes is about 20 nm. The same method can be used to calculate the closest separation of nanotubes with any geometry. An alternative method can be used to calculate the electric field in the vicinity of two closely spaced nanotubes and reduce the spacing until the calculated electric field has a distribution that would exclude deposition of a third nanotube in between the two that are already deposited.

Once the closest separation (s) between nanotubes is known, the number of nanotubes, N, deposited in the slot is given by: N=MOD(L/s). The function MOD( ) truncates the resulting number L/s to an integer. The shape at the ends of the slot may also modify this result, depending on the degree of rounding. The calculation is most accurate if there is no rounding. With the presence of rounding, an additional degree of focusing may reduce the number of deposited nanotubes, and this can be determined using three dimensional finite element analysis for the exact geometry.

As shown above, embodiments of the present invention provide a method for controllable depositing nanotubes using electrophoresis in a defined region. The deposition region may be defined by an aperture, which can be configured to control the number of nanotubes that can be deposited in the region, as well as the spacings of deposited nanotubes. By properly configuring the aperture, e.g., providing a sufficiently small aperture size such as less than about 100 nm, one can also control the deposition such that only a single nanotube is deposited in the region, with lateral alignment precision of a few nanometers.

Embodiments of the invention provide a room temperature process that is readily scalable and compatible with conventional fabrication processes and materials, and allow improved control over the properties of nanotubes being used in device fabrication.

Although some examples have been discussed in the context of the deposition of carbon nanotubes, it is understood that the method can generally be adapted for deposition of other nanotubes. Furthermore, embodiments of the invention can generally be applied to depositing single-walled, multi-walled, semiconducting or metallic nanotubes for fabrication of different devices.

While the foregoing is directed to embodiments of the present invention, other and further embodiments of the invention may be devised without departing from the basic scope thereof, and the scope thereof is determined by the claims that follow.

The invention claimed is:

1. A method of depositing nanotubes, comprising:
   (a) defining a region on a structure by an aperture;
   (b) configuring the aperture to control a number of nanotubes to be deposited by electrophoresis in the region; and
   (c) depositing the number of nanotubes in the region by electrophoresis;
   wherein the aperture is configured as a slot having a width of less than about 100 nm, and a length sufficiently large to allow deposition of at least two nanotubes along a direction of the length.

2. The method of claim 1, wherein step (b) further comprises:
   configuring the aperture to control at least one of a pattern and spacing of nanotubes to be deposited in the region.

3. The method of claim 1, wherein step (b) further comprises:
   providing the aperture with a combination of length, width and depth to control the number of nanotubes to be deposited.

4. The method of claim 1, wherein step (b) further comprises:
   providing the aperture with a lateral dimension to allow only one nanotube to be deposited in the region by electrophoresis.

5. The method of claim 4, wherein the lateral dimension of the aperture is less than about 100 nm.

6. The method of claim 1, wherein step (b) further comprises:

(b1) performing finite element analysis as a function of at least one parameter of the aperture to obtain an electric field distribution in proximity of the aperture; and (b2) selecting a configuration of the aperture suitable for depositing the number of nanotubes in the region.

7. The method of claim 6, wherein at least one parameter for the nanotubes to be deposited is included in the finite element analysis.

8. The method of claim 1, wherein the nanotube is a carbon nanotube.

9. The method of claim 1, wherein: step (a) further comprises:
(a1) providing the structure with an insulating layer over a metal layer; and
(a2) forming the aperture through the insulating layer to define the region at the metal layer.

10. The method of claim 9, wherein step (c) further comprises:
(c1) exposing the structure to an electrolytic fluid containing nanotubes;
(c2) applying a bias voltage to the metal layer; and
(c3) depositing the number of nanotubes in a vertical orientation to contact the metal layer inside the aperture.

11. The method of claim 10, wherein the number of nanotubes is one.

12. The method of claim 11, wherein the nanotube is deposited to be substantially centered inside the aperture.

13. The method of claim 10, wherein step (c) further comprises:
(c4) providing a metal electrode in the electrolytic fluid; and
(c5) providing a positive bias to the metal electrode relative to the metal layer.

14. A method of depositing nanotubes, comprising:
(a) defining a region on a structure by an aperture, which step of defining includes providing the structure with an insulating layer over a metal layer; and forming the aperture through the insulating layer to define the region at the metal layer;
(b) configuring the aperture to control a number of nanotubes to be deposited by electrophoresis in the region;
(c) depositing the number of nanotubes in the region by electrophoresis, which step of depositing includes exposing the structure to an electrolytic fluid containing nanotubes; providing a metal electrode in the electrolytic fluid; and providing a positive bias to the metal electrode relative to the metal layer; applying a bias voltage to the metal layer; and depositing the number of nanotubes in a vertical orientation to contact the metal layer inside the aperture; and
(d) controlling orientations of the nanotubes inside the aperture by adjusting an orientation of the metal electrode relative to the metal layer.

15. The method of claim 1, wherein the aperture has a height to width ratio of at least about 0.18.

16. A method of forming a carbon nanotube-based device, comprising:
providing a substrate with an insulating layer formed on a conductive layer;
forming an aperture through the insulating layer to expose a region of the conductive layer;
immersing the substrate in an electrolytic fluid containing carbon nanotubes;
providing a metal electrode in the electrolytic fluid;
applying a bias voltage across the conductive layer and the metal electrode; and
depositing at least one carbon nanotube in a substantially perpendicular orientation with respect to the region, wherein one end of the carbon nanotube contacts the region proximate a center of the region;
providing the substrate with the at least one deposited carbon nanotube to a plasma process system for further processing; and
re-aligning the at least one deposited carbon nanotube to a desired orientation by applying an electric field between the conductive layer and an electrode in the plasma process system.

17. The method of claim 14, wherein the aperture is configured as a slot having a width of less than about 100 nm, and a length sufficiently large to allow deposition of at least two nanotubes along a direction of the length.

18. The method of claim 14, wherein the aperture has a height to width ratio of at least about 0.18.

19. The method of claim 14, wherein the number of nanotubes is one.

20. The method of claim 19, wherein the nanotube is deposited to be substantially centered inside the aperture.

* * * * *